(12) United States Patent
Fawcett et al.

(10) Patent No.: US 6,240,984 B1
(45) Date of Patent: Jun. 5, 2001

(54) FOOT SEAL FOR LIQUID HANDLER

(75) Inventors: Kevin Richard Fawcett, Ridgeway, WI (US); John Paul Hlavachek, Worcester, MA (US); Craig A. Schultz, Madison, WI (US)

(73) Assignee: Gilson, Inc., Middleton, WI (US)

( * ) Notice: Subject to any disclaimer, the term of this patent is extended or adjusted under 35 U.S.C. 154(b) by 0 days.

(21) Appl. No.: 09/520,384

(22) Filed: Mar. 8, 2000

(51) Int. Cl.$^7$ ..................................................... B65B 43/42
(52) U.S. Cl. ........................ 141/130; 141/129; 422/100
(58) Field of Search ............................. 141/130, 94, 156, 141/157, 159, 160, 129, 178, 237, 238, 242, 244, 263, 264, 291, 295; 73/863.32, 863.1; 422/100, 101, 102, 65; 222/137, 402.24

(56) References Cited

U.S. PATENT DOCUMENTS

| | | | |
|---|---|---|---|
| 2,503,147 | * | 4/1950 | Applezeig . |
| 3,289,712 | * | 12/1966 | Smith . |
| 4,265,855 | * | 5/1981 | Mandle et al. ........................... 422/65 |
| 4,478,095 | * | 10/1984 | Bradley et al. .................... 73/864.23 |
| 4,577,514 | * | 3/1986 | Bradley et al. .................... 73/863.01 |
| 4,669,321 | * | 6/1987 | Meyer . |
| 4,810,471 | * | 3/1989 | Wachob et al. ....................... 422/101 |
| 4,951,512 | * | 8/1990 | Mazza et al. ..................... 73/861.23 |
| 4,962,041 | * | 10/1990 | Roginski ................................ 422/63 |
| 5,935,523 | * | 8/1999 | McCandless et al. ............... 422/100 |

* cited by examiner

Primary Examiner—Steven O. Douglas
Assistant Examiner—Khoa Huynh
(74) Attorney, Agent, or Firm—Mason, Kolehmainen, Rathburn & Wyss; Philip M. Kolehmainen

(57) ABSTRACT

An automated liquid handler includes a probe assembly with a probe foot that can be moved down against the top of sample containers of a variety of sizes and shapes defined by racks, tubes or plates. A seal at the bottom of the foot provides a seal between the foot and the containers making it possible to prepare a SPE sample by using positive, probe introduced pressure within the containers to force liquid samples out through media at the bottom of the container. The foot seal is self sealing without the need for adhesives or other potential contaminates, and is removeably mounted to the probe foot.

9 Claims, 5 Drawing Sheets

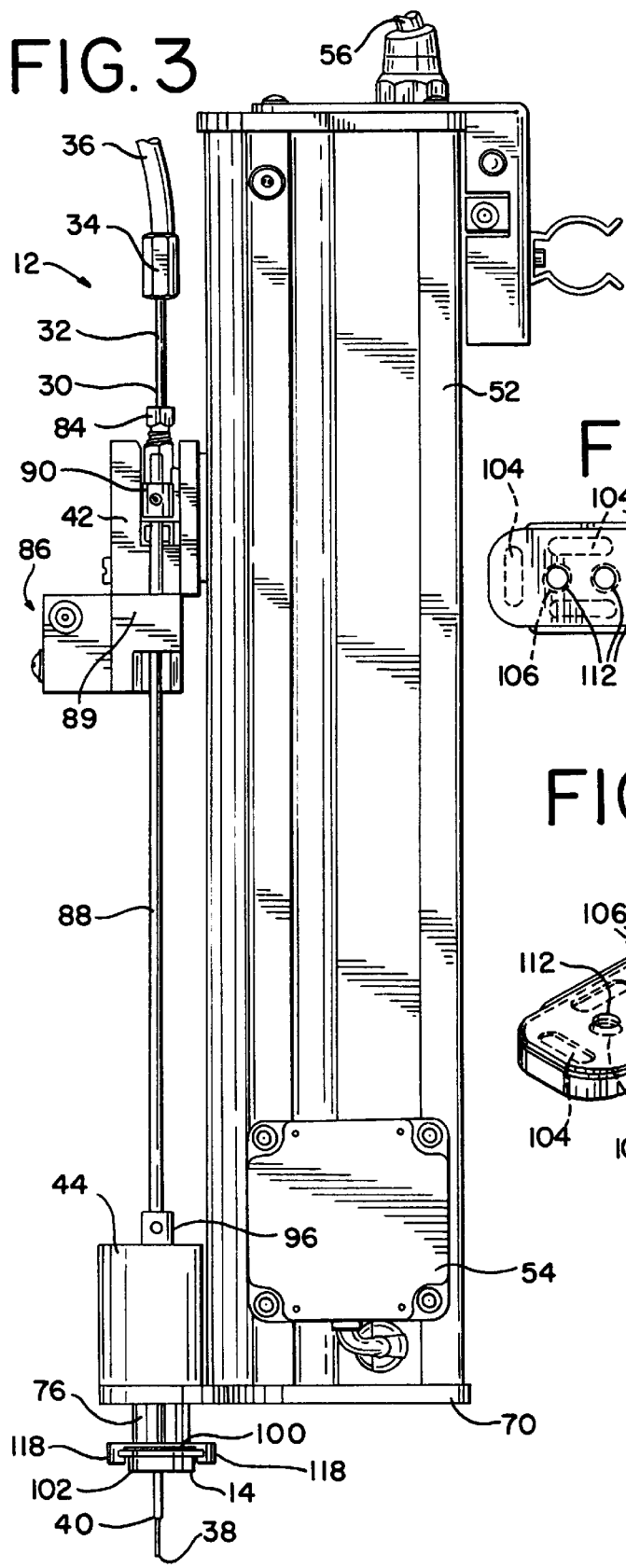
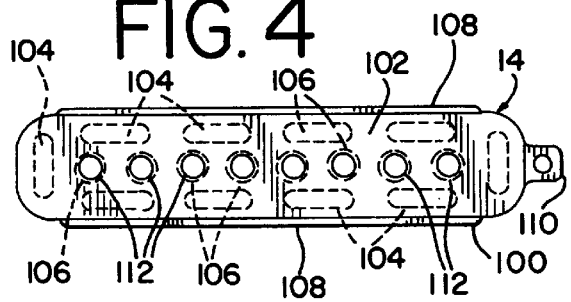
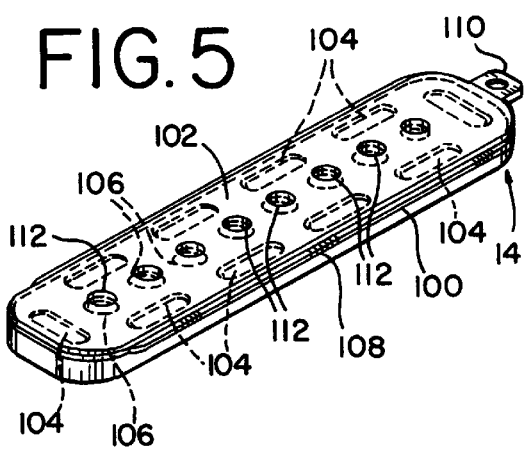

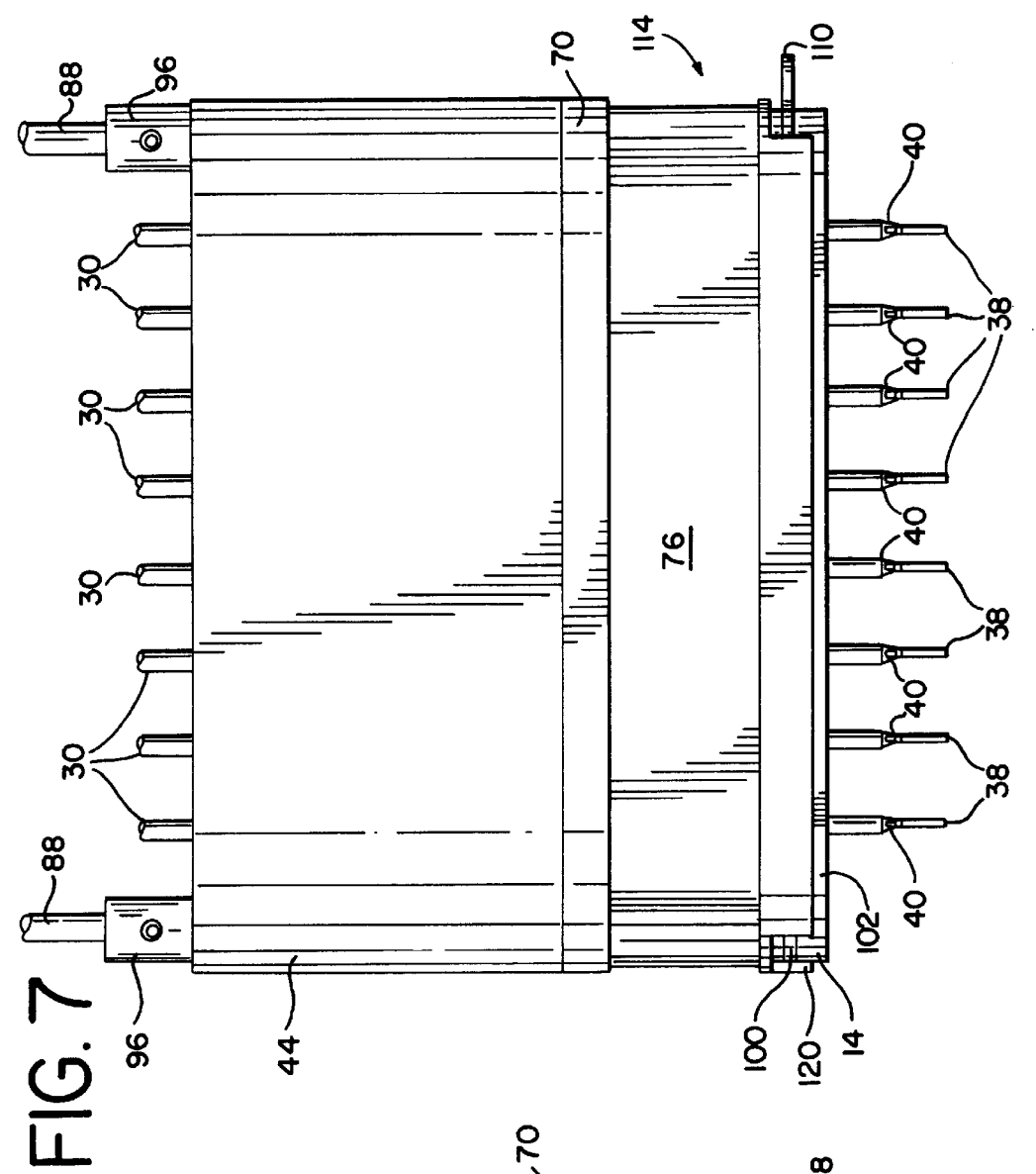
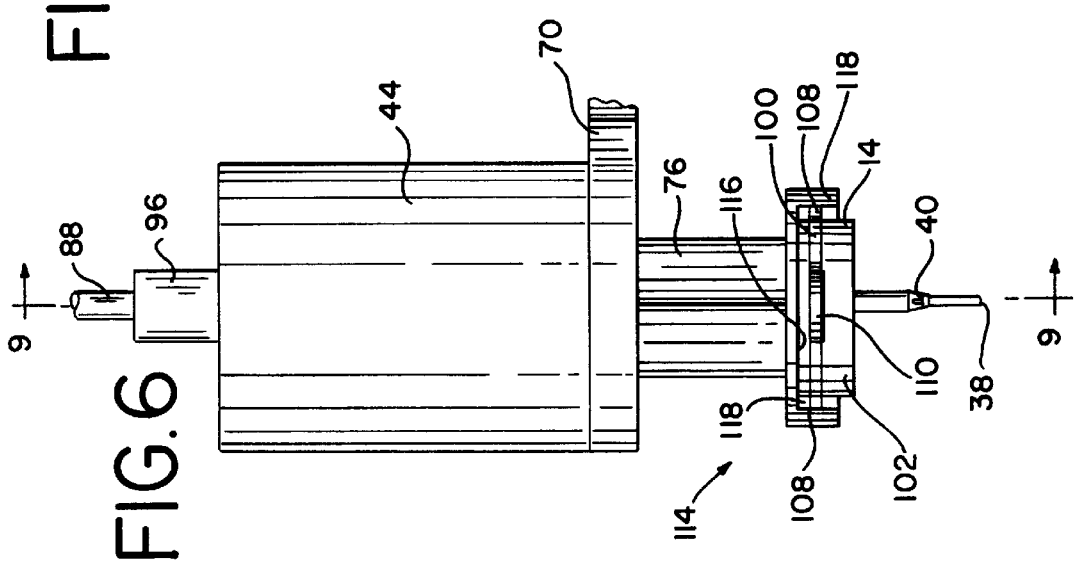

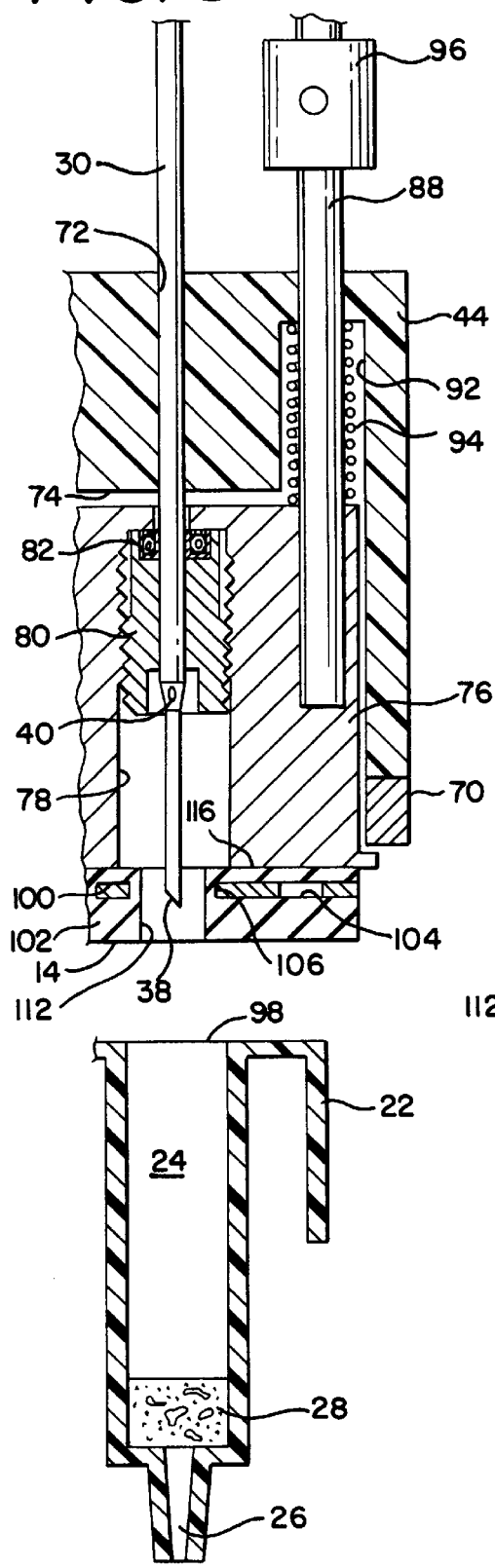
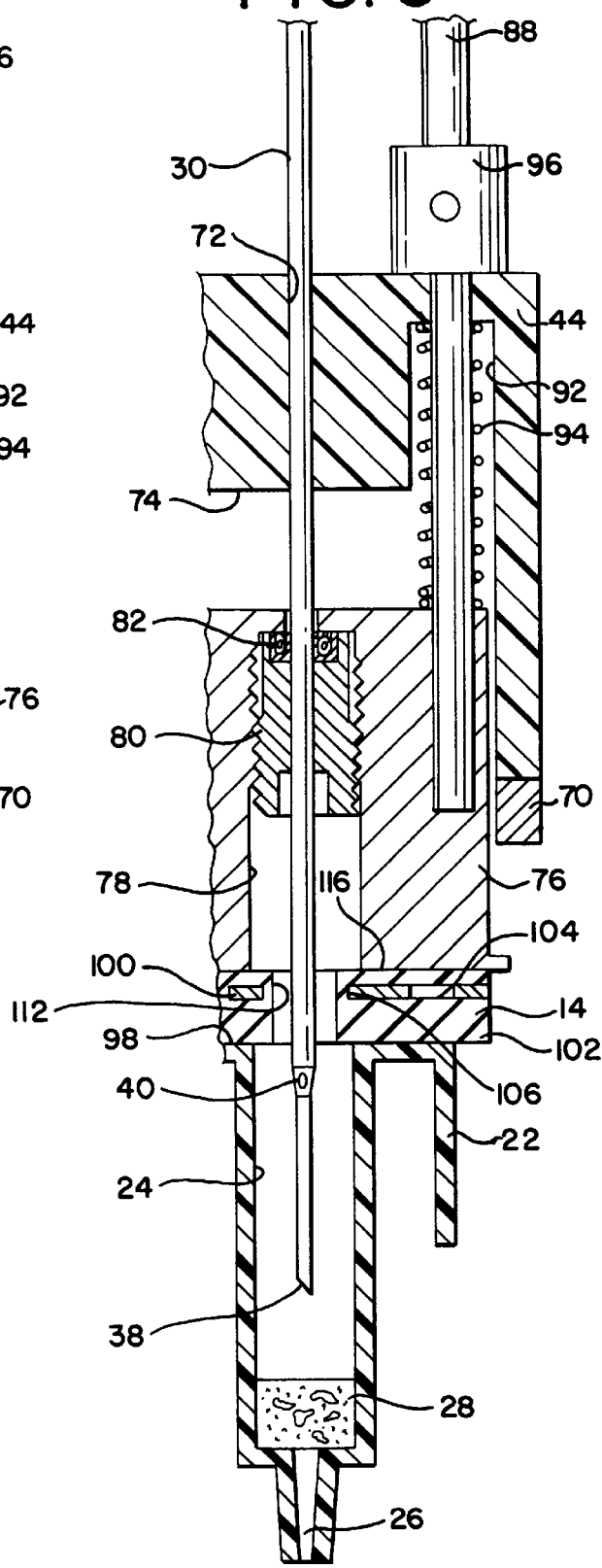

FOOT SEAL FOR LIQUID HANDLER

FIELD OF THE INVENTION

The present invention relates to automated liquid handlers and more particularly to an improved probe assembly having a foot seal for sealing the interface between the probe foot and the tops of sample containers accessed by the probes of the probe assembly

DESCRIPTION OF THE PRIOR ART

Automated liquid handlers are used for handling laboratory samples in a variety of laboratory procedures. In solid phase extraction (SPE) procedures, a solid medium in a sample container is covered with a liquid that is introduced into the container by a probe, and the liquid is removed from the container through a sorbent packing covering a discharge passage at the bottom of the sample container. Although the liquid can be permitted to drain using only the force of gravity, this is a slow process and prevents high throughput automated SPE analysis.

In order to increase the speed of the SPE procedure, a pressure differential can be applied so that the interior of the sample container is at a higher pressure than the region outside the container discharge passage As a result, the liquid discharge flow rate is increased. The desired pressure differential can be imposed by application of vacuum to the region below the sample containers. However a more effective and more precisely controlled approach is to apply increased pressure within the containers. This can be done by using a probe having two axially extending passages, one for the liquid to be introduced into the sample container, and another for the introduction of a pressurized inert gas for pressurizing he container.

In order to permit an elevated pressure within the container, the top of the container must be sealed from the surrounding atmosphere. In addition, the probe must be able to enter the container without interfering with the sealing effect. Sample containers of many configurations and sizes are available, ranging from tubes or vessels of various cross sectional shapes to microplates having numerous sample containing wells in arrays having, for example, 96 or 384 wells. It would be desirable to provide a probe assembly able to provide a seal with many different types of sample container. A further difficulty arises from the fact that liquid handlers can be provided with multiple probes, such as eight probes, that simultaneously operate with a similar number of sample containers. An effective probe assembly sealing arrangement should be able to accommodate both single and multiple probe arrangements with various numbers of probes at various centerline spacings.

One approach that has been used in the past is to mount a sealing member on the probe so that when the probe is inserted into a sample container, the seal member also enters the container to provide a seal between the probe and the inner wall of the container. For multiple probe assemblies, each probe is supplied with a discrete seal member. The difficulty with this approach is that the seal body, or each seal body in a multiple probe system, must mate precisely with the sample containers. The seals and sample containers must be uniform in size and shape. The seal body cannot be used with other types of sample containers having different shapes or sizes.

Another approach that has been used in the past is to manually insert a seal body into the top of each sample container. These seal bodies have apertures through which the probe can be inserted into the sample container. After the probe is inserted, the seal body provides a seal between the probe and the wall of the container. A difficulty with this approach is that the seal insertion step requires slow and burdensome manual labor. In addition, the seal bodies must be matched to specific container types.

SUMMARY OF THE INVENTION

A principal object of the present invention is to provide an improved foot seal for automated liquid handlers. Other objects are to provide a foot seal that functions without alteration or special preparation with sample containers of many types, sizes and shapes; to provide a foot seal that is self sealing without special preparative steps; to provide a foot seal that is easily and replaceably mounted on a probe foot; and to provide an automated liquid handler having a probe foot seal overcoming disadvantages of probe sealing systems used in the past.

In brief, in accordance with the invention there is provided a solid phase extraction probe assembly for use with a sample container having a horizontal container top surface. The assembly includes a vertically extending, elongated probe and a foot defining a probe receiving passage extending from the top to the bottom of the foot. Support means for supports the foot, and drive means moves the support means and the foot relative to the sample container array, and moves the probe axially through the foot receiving passage in the foot. A foot seal is attached to the bottom of the foot, the foot seal having a probe receiving opening aligned with the probe receiving passage. The foot seal has an upper surface in sealing relation against the bottom surface of the foot and a lower surface engageable in sealing relationship with the container top surface.

BRIEF DESCRIPTION OF THE DRAWING

The present invention together with the above and other objects and advantages may best be understood from the following detailed description of the preferred embodiment of the invention illustrated in the drawings, wherein:

FIG. 3 is a view like FIG. 2 with the probes in an extended position;

FIG. 4 is a bottom elevational view of the foot seal of the liquid handler;

FIG. 5 is an isometric view of the foot seal;

FIG. 6 is a further enlarged side view of the lower portion of the probe assembly with the probes in the extended position;

FIG. 7 is a front view of the lower portion of the probe assembly as seen in FIG. 6;

FIG. 8 is an enlarged sectional view like FIG. 9 illustrating a probe in the retracted position before accessing a sample containing receptacle in a receptacle rack; and FIG. 9 is an enlarged cross sectional view taken along the line 9—9 of FIG. 6 illustrating the probe assembly in engagement with a rack of receptacles during a SPE procedure.

DETAILED DESCRIPTION OF THE PREFERRED EMBODIMENTS

Figure 1:
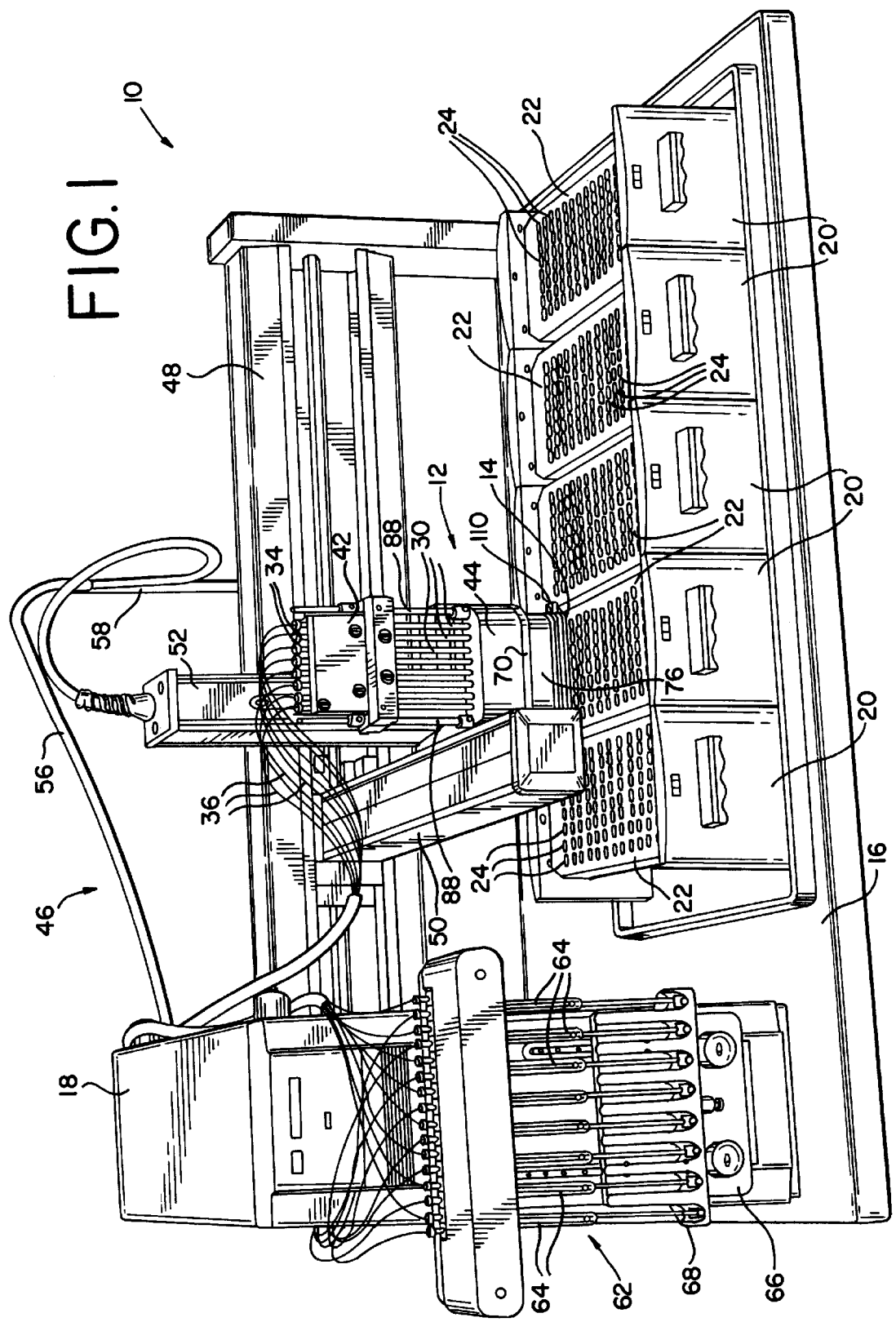
FIG. 1 is a perspective view of an automated liquid handler having a foot seal constructed in accordance with the present invention.

Having reference now to the drawings, in FIG. 1 there is illustrated an automated liquid handler designated as a whole by the reference numeral 10. In accordance with the present invention, the liquid handler 10 includes a probe assembly generally designated as 12 including a foot seal 14 providing advantages when the liquid handler 10 is used for solid phase extraction (SPE) procedures.

The automated liquid handler 10 seen in FIG. 1 is configured for SPE operations and includes a base 16 with a housing 18 at one end. The base 16 supports a tray 20 supporting racks 22 each holding or defining numerous SPE sample containers 24 such as wells or receptacles. In the illustrated embodiment, the racks 22 are molded plastic with an eight by twelve array of 96 integral sampler receptacles 24. Other alternatives such as microplates and other arrays such as racks or plates with, for example, 380 receptacles or sample containing wells are also possible. The sample containers 24 also can be separate tubes or the like supported in a tray. As seen in FIGS. 8 and 9, each receptacle 24 includes a bottom exit port 26 covered by a body 28 of filter material or sample collecting media.

The probe assembly 12 preferably includes multiple probes 30. In the illustrated arrangement, there are eight probes having a spacing equal to the spacing of a row of sample containers 24 in the racks 22. Other arrays such as four or two or single probes is possible. Each probe 30 is a double walled hollow tube defining an inner, liquid conducting passage surrounded by an annular outer pressurizing passage. The top of each probe includes an upward extension 32 of the liquid passage provided with a fitting 34 through which liquid can be introduced or extracted through a flexible conduit 36. The bottom of each probe 30 includes an open tip 38 at the lower end of the liquid passage. The outer passage at its upper end communicates within the probe holder 42 with a pressure chamber providing a selectively applied source of pressurized inert gas such as argon. At its lower end, the outer, pressurizing passage terminates above the tip 38, and is provided with a port 40 through which pressure may be applied to the interior of the sample containers 24.

The probe assembly includes a vertically movable probe holder 42 that holds the probes 30 for simultaneous movement. The lower ends of the probes 30 are guided by a probe guide 44. The probe assembly 12 is moved relative to the tray 20 and the racks 22 by a transport system 46 including an X drive arm 48, a Y drive arm 50 and a Z drive arm 52. The transport system 46 locates the probes 30 precisely in a three coordinate system including X, Y and Z coordinates. The probes 30 can be located by the X and Y drive arms above any corresponding sample containers 24, and the probes 30 can be raised and lowered relative to the containers 24 by the Z drive arm 52.

Figure 2:
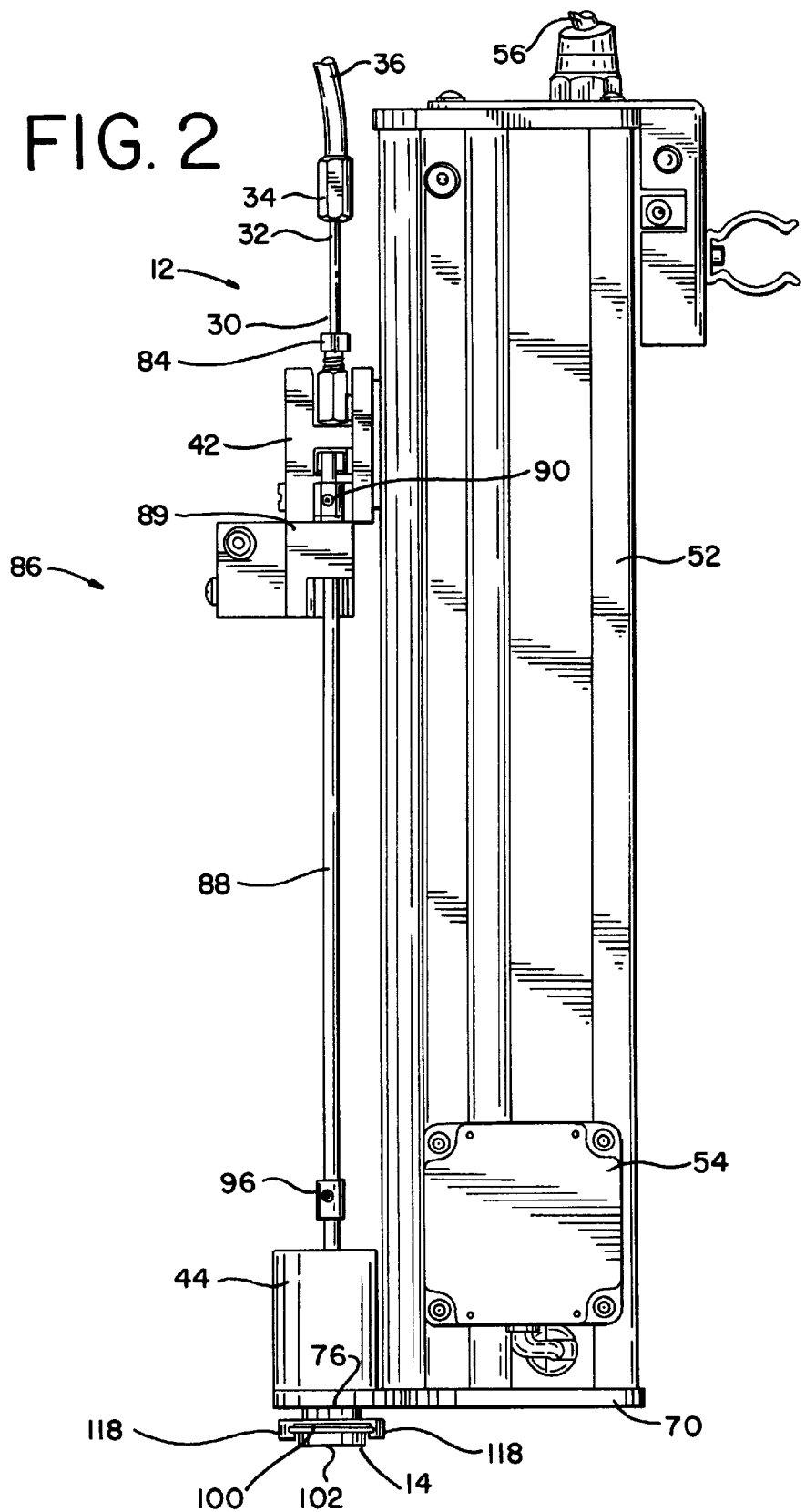
FIG. 2 is a side elevational view on an enlarged scale of the Z drive arm and probe assembly of the liquid handler of FIG. 1 with the probes in a retracted position.

The X drive arm 48 is supported in a fixed position extending behind and above the tray 20 from the housing 18. The Y drive arm 50 extends forward from the X drive arm 48 over the tray 20. An X drive motor associated with the X drive arm 38 moves the Y drive arm 50 in the X direction along the length of the tray 20. The Z drive arm 52 is supported by the Y drive arm 50 and extends vertically in the Z direction. A Y drive motor associated with the Y drive arm 50 moves the Z drive arm 52 in the Y direction across the width of the tray 20. The probes 30 in the probe holder 42 are carried by the Z arm 52 and are moved in the vertical Z direction by a Z drive motor 54 (FIGS. 2 and 3) supported by the Z drive arm 52. A Z drive control cable 56 supported by a rod 58 extends from the housing 20 to the Z drive arm 42. A liquid level sensing cable 60 extends between the Z drive arm 52 and the probe holder 42. A further description of the transport system 36 and other elements of the liquid handler 10 beyond that helpful to an understanding of the present invention can be found in U.S. Pat. No. 4,422,151, incorporated herein by reference.

A syringe pump assembly 62 includes a ganged array of syringe pumps 64, each communicating through one of the conduits 36 with one of the probes 30. The syringe pump 64 can be placed in communication with a reservoir or with the probes 30. When the syringe pumps 64 communicate with the probes 30, they can be operated in one direction to decrease pressure at the probes to draw liquid, for example a sample for SPE analysis, into the probe. The syringe pumps 64 can be operated in the other direction to increase pressure at the probes 30 to expel liquid from the probe into a sample container 24. The assembly 30 includes a fixed support 66 and a motor driven slide or carriage 68 respectively supporting a pair of cooperating pumping members of the syringe pumps 64. A further description of the syringe pump assembly 62 beyond that helpful to an understanding of the present invention can be found in U.S. Pat. No. 5,988,236 issued Nov. 23, 1999, incorporated herein by reference.

Referring more specifically to the probe assembly 12, the Z drive arm 52 includes a base plate 70 to which the probe guide 44 is fastened. The probe guide 44 includes eight vertically extending guide passages 72 (FIGS. 8 and 9), one slideably receiving one of the probes 30. A probe foot cavity 74 is defined in the bottom of the probe guide 44 and a probe foot 76 is received in the cavity 74 for limited vertical movement relative to the probe guide 44. The probe foot 76 includes eight vertically extending probe receiving openings 78 aligned with the probe guide passages 72 and each receiving one of the probes 30. A gas tight seal is formed between the probe foot 76 and each of the probes 30 by a seal holder 80 threaded into each opening 78 and a seal assembly 82 slideably receiving the corresponding probe 30. Preferably the assembly 82 is a BAL seal part number C-101MB-(0.072)-GC-(W0.057)-316 available from the Bal Seal Engineering company, Inc. 19650 Pauling, Foothill Ranch, Calif. 92610 U.S.A.

The probe holder 42 is movable by the Z drive motor 54 by a drive system within the Z drive arm 52 in the vertical or Z direction relative to the base plate 70 and the probe guide 44. The probes 30 are attached by lugs 84 (FIGS. 1–3) to the probe holder 42 and move together with the probe holder 42. A lost motion drive system 86 including a pair of lifting rods 88 provides a lost motion connection between the probe holder 42 and the probe foot 76 so that certain limited vertical motion is transferred from the probe holder 42 to the probe foot 76.

The lifting rods 88 are aligned with the probes 30, and one is located at each side of the probe assembly 12. The rods 88 slideably extend through openings in a lifting block portion 89 of the probe holder 42. Upper stop collars 90 are contacted by the lifting block 89 when it moves upward (FIG. 2) and are spaced from the lifting block 89 when it moves downward (FIG. 3). The lower ends of the lifting rods 88 are attached to the probe foot 76. A pair of spring receiving cavities 92 extend upwardly from the probe foot cavity 74, each receiving a spring 94 that biases the probe foot 76 downward and away from the probe guide 44. A lower stop collar 96 on each lifting rod 88 is engageable by the top of the probe guide 44 and establishes a maximum spacing between the probe foot 76 and the probe guide 44. Additional springs may be placed in compression between the probe guide 44 and the probe foot 76.

The lost motion drive system 86 permits the liquid handler 10 to perform SPE procedures with samples placed within the sample containers 24. Initially the probe assembly 12 is in a normal or standby position (FIGS. 2 and 8) with the probe holder 42 lifted by the Z drive motor 54 to an upper position seen in FIG. 2. The probe holder lifting block 89 engages the upper stop collars 90 and the lifting rods 88 lift the probe foot 76 to a retracted position (FIG. 8) wherein the springs 94 are compressed. In this position, the probes 30 are retracted upward into the probe foot 76 and probe guide 44 and the lower stop collars 96 are spaced above the probe guide 44.

With the probe assembly in this normal condition, the transport system 46 is operated to align the probes 30 with a selected group of eight sample containers 24 in one of the racks 22 upon the tray 20. This aligned position with the probes 30 located directly above selected sample containers 24 is seen in FIG. 8. Then the probe holder 42 is moved downward by the Z drive motor 54 toward the base plate 70 and the probe guide 44.

In the initial part of this downward motion, as the lower stop collars 96 move down into contact with the probe guide 44, the springs 94 force the probe foot 76 down and away from the probe guide 44 and vertically fixed base plate 70. In the absence of a rack 22 and sample containers 24, the foot 76 can move a substantial distance down within the probe foot cavity 74 (see FIGS. 3, 6 and 7). When the probe assembly is aligned with containers 24 in a rack 22, the foot seal 14 engages a top surface 98 of the rack before the full range of movement of the foot 76 can occur. As a result, the springs 94 remain compressed in order to resiliently urge the foot seal 14 down in sealing relation with the containers 22.

As the downward motion of the probe holder 42 continues, the positions of the probe holder 44 and foot 76 relative to the rack 22 does not change and the foot seal continues to seal against the top surface 98. The lost motion drive system 86 permits the probe holder 42 to move further downward as the lifting block 89 moves down and away from the upper stop collars 90 (FIG. 3). The probes 30 move down along with the probe holder 42, into an extended position where they project downward from the probe foot 76 (FIGS. 3, 6, 7 and 9). In this position, the probe tip 38 is received within a sample container 24 (FIG. 9) in a position to add (or remove) liquid from the sample container 24.

When the foot seal is in contact with the top surface 98 of the container 24 or rack 22, a sealed pressure chamber is defined by the interior of the container 24 and by the aligned corresponding probe receiving opening 78. This chamber is sealed from atmosphere by the seal assembly 82 and by contact of the foot seal 14 against the top surface 98 and against the bottom surface of the probe foot 76. The pressure port 40 is located within this chamber, below the seal assembly 82. As a result, the outer, pressurizing passage of the probe 30 can pressurize the interior of the sample container 24.

The foot seal 14 is provided in accordance with an important feature of the present invention. The seal 14 is shaped to generally conform to the bottom of the probe foot 76 and includes a flat metal support plate 100 to which is bonded an elastic resilient seal body 102. The plate 100 can be stamped and formed from 20 gauge (0.036") 2b stainless steel sheet material. The plate 100 is provided with a number of oval-shaped lock openings 104 and with eight oversized probe openings 106 having the same center-to-center spacing as the probes 30, the probe guide openings 72 and the probe receiving openings 78. The opposed side edges of the plate 100 define laterally projecting guide wings 108, and an apertured tang 110 extends from an end of the plate 100.

The seal body 102 can be molded of silicone rubber in the 10–20 durometer hardness range and is molded in place around the plate 100. The material of the body 102 fills the lock openings 104 and partly fills the oversized probe openings 106 in order to create a secure mechanical interlock of the body 102 to the plate 100. Probe passages 112 are defined by the body 102 concentric within the openings 106, and the wings 108 and tang 110 project out of the body 102.

A nest 114 is defined at the bottom of the probe foot 76 for removeably receiving the foot seal 14. The probe receiving openings 78 terminate at a flat bottom wall surface 116 of the probe 76 flanked by a pair of opposed guide channels 118 extending along the sides of the probe foot 76. The seal body 102 is thinner at the top side of the plate 100 and thicker at the bottom side, and when correctly oriented, the foot seal is inserted into place with a sliding motion with the wings 108 received in the channels 118. A tab 120 stops the foot seal in its fully inserted position by engaging the end of the foot seal 14 opposite the tang 110. The tang facilitates removal of the foot seal from the nest 114. In the inserted position, the seal body is slightly compressed against the bottom wall surface 116 of the probe foot 76 to provide both an initial seal and a frictional locking effect holding the foot seal 14 in place.

In use, when the seal foot is moved downward into engagement with the top surface of a rack 22 or of containers 24, the relatively thicker lower part of the seal body provides ample resilience to conform to irregular surfaces. The foot seal can accommodate containers of various shapes such as square or round and of a wide range of sizes. It can provide a seal with microtiter plates or well blocks of many configurations or with integral racks such as the illustrated racks 22 (see FIG. 9) or with discrete tubes and containers of many configurations. For larger containers or containers having larger centerline spacings, the seal body 102 can be molded to fill selected ones of the oversized holes 106 in the plate 100, leaving, for example, four or two or one probe passage 112 spaced to accommodate a matching number of probes in the probe assembly 12.

When the liquid handler 10 is used to perform a SPE procedure and the probe foot 76 is biased against the top surface 98 of the rack 22, the seal body 102 remains compressed against the probe bottom surface 116 and is further compressed against the top surface 98 providing a secure and reliable seal between the probe foot 76 and the sample containers. There is no adhesive or the like needed in the system and possible sample contamination is avoided. There is no need to change or tailor the system for different sizes, shapes or types of sample containers, and the self sealing takes place automatically without the need for premounting seals on the rack or other time consuming preparative operations. When the interior of the sample container is pressurized, the liquid sample is driven by positive pressure through the media 28 and out of the exit port 26. The seal foot 14 makes it easy and practical to enjoy the advantages of positive pressure sample displacement in a high throughput system and avoid the disadvantages of systems using vacuum under the sample containers for sample displacement.

While the present invention has been described with reference to the details of the embodiment of the invention shown in the drawing, these details are not intended to limit the scope of the invention as claimed in the appended claims.

What is claimed is:

1. A solid phase extraction probe assembly for use with a sample container having a horizontal container top surface, said assembly comprising:

a vertically extending, elongated probe;

a foot defining a probe receiving passage extending from the top to the bottom of said foot;

support means for supporting said foot and drive means for moving said support means and said foot relative to the sample container array, and for moving said probe axially through said foot receiving passage in said foot;

a foot seal attached to the bottom of said foot, said foot seal having a probe receiving opening aligned with said probe receiving passage; and said foot seal having an upper surface in sealing relation against the bottom surface of said foot and a lower surface engageable in sealing relationship with the container top surface;

said foot seal further including a metal support plate enclosed at least partly within said molded body.

2. A solid phase extraction probe assembly as claimed in claim 1, said probe receiving opening being larger than the diameter of said probe, and said foot including a probe seal in said passage in sealing contact with the wall of said passage and with the wall of said probe.

3. A solid phase extraction probe assembly as claimed in claim 1, said foot seal including a molded body of flexible, resilient material.

4. A solid phase extraction probe assembly as claimed in claim 1, said foot defining a mounting nest including a pair of guide channels and said support plate including wings projecting from said body and slideably received in said channels.

5. A solid phase extraction probe assembly as claimed in claim 1, said probe having a first passage for the travel of liquid through said probe and a second passage for the application of gas pressure through said probe.

6. A probe assembly for use with an automated multiple probe liquid handler and an array of sample containers, said probe assembly comprising:

a plurality of probes having lower probe tips and upper portions;

a probe guide having a plurality of vertically extending passages for guiding said probes;

a probe holder carrying said upper portions of said probes and being mounted for vertical movement relative to said probe guide;

a probe foot supported at the bottom of said probe guide for vertical movement relative to said probe guide, said probe foot having a bottom surface and probe passages intersecting said bottom surface;

a drive system connected between said probe holder and said probe foot for moving said probe foot in response to movement of said probe holder;

a seal nest defined at the lower portion of said probe foot; and a foot seal mounted in said seal nest, said foot seal having a plurality of apertures each receiving one of said probes, an upper seal surface in sealing engagement with said probe foot bottom surface, and a lower seal surface adapted to move into sealing relation with said array of sample containers;

said foot seal comprising a support plate and an elastomeric sealing body molded over said support plate.

7. A probe assembly as claimed in claim 6, said support plate having locking openings filled by said overmolded body.

8. A probe assembly as claimed in claim 7, said seal nest including a pair of opposed channels, and said support plate including a pair of wings projecting from said body and slideably received in said channels.

9. A probe assembly as claimed in claim 6, said probes being double walled and including a liquid passage and a pressure passage.

* * * * *